United States Patent
Leon et al.

(10) Patent No.: US 11,234,389 B2
(45) Date of Patent: *Feb. 1, 2022

(54) NUCLEOTIDE SEQUENCES MUTATED BY INSERTION THAT ENCODE A TRUNCATED OLEATE DESATURASE PROTEIN, PROTEINS, METHODS AND USES

(71) Applicant: Advanta Holdings BV, Breda (NL)

(72) Inventors: Alberto Javier Leon, Buenos Aires (AR); Andrés Daniel Zambelli, Buenos Aires (AR); Roberto Juan Reid, Buenos Aires (AR); Monica Mariel Morata, Buenos Aires (AR); Marcos Kaspar, Buenos Aires (AR)

(73) Assignee: Advanta Holdings BV, Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/164,696

(22) Filed: Oct. 18, 2018

(65) Prior Publication Data

US 2019/0037791 A1 Feb. 7, 2019

Related U.S. Application Data

(63) Continuation of application No. 13/822,279, filed as application No. PCT/EP2011/061165 on Jul. 1, 2011, now Pat. No. 10,143,149.

(51) Int. Cl.
| | |
|---|---|
| *A01H 6/14* | (2018.01) |
| *A01H 1/00* | (2006.01) |
| *A01H 5/10* | (2018.01) |
| *C12N 15/82* | (2006.01) |

(52) U.S. Cl.
CPC .............. *A01H 6/14* (2018.05); *A01H 1/104* (2021.01); *A01H 5/10* (2013.01); *C12Y 114/19006* (2013.01); *C12N 15/8247* (2013.01)

(58) Field of Classification Search
CPC .............................. A01H 5/10; C12N 15/8247
See application file for complete search history.

(56) References Cited

U.S. PATENT DOCUMENTS

| | | | |
|---|---|---|---|
| 4,627,192 A | 12/1986 | Fick | |
| 10,143,149 B2* | 12/2018 | Leon | ........................ A01H 5/10 |
| 2009/0307806 A1* | 12/2009 | Falentin | ............... C12N 9/0083 800/298 |
| 2012/0023601 A1 | 1/2012 | Leon et al. | |

OTHER PUBLICATIONS

Patel et al (High-oleate peanut mutants result from a MITE insertion into the FAD2 gene. Theor Appl Genet. 108:1492-1502, 2004) (Year: 2004).*
Schuppert et al (The sunflower high-oleic mutant OI carries variable tandem repeats of FAD2-1, a seed-specific oleoyl-phosphatidyl choline desaturase. Molecular Breeding 17: 241-256, 2006) (Year: 2006).*
Long et al (Identification and Functional Analysis of Two New Mutant BnFAD2 Alleles That Confer Elevated Oleic Acid Content in Rapeseed. Front. Genet., 20, 1-12, 2018) (Year: 2018).*
Lacombe et al (An insertion of oleate desaturase homologous sequence silences via siRNA the functional gene leading to high oleic acid content in sunflower seed oil. Mol Genet Genomics. 281:43-54, 2009). (Year: 2009).*
Lacombe et al.. An insertion of oleate desaturase homologous sequence silences via siRNA the functional gene eading to high oleic acid content in sunflower seed oil. Mol Genet Genomics. 281:43-54, 2009.
Patel et al., High-oleate peanut mutants result from a MITE insertion into the FAD2 gene. Theor Appl Genet. 108:1492-1502, 2004.
Schuppert et al., The sunflower high-oleic mutant OI carries variable tandem repeats of FAD2-1, a seed-specific oleoyl-phosphatidyl choline desaturase. Molecular Breeding. 17:241-256,2006.
Frankel et al., Characterization of diphtheria fusion proteins targeted to the human interleukin-3 receptor, Protein Eng. Aug. 2000; 13(8):575-81.
Martinez-Rivas et al., Delta 12-oleate desaturase [Melianthus annuus], GenBank: AAL68981.1,2002, 1 page.
Hongtrakul et al., A Seed Specific Delta-12 Oleate Desaturase Gene is Duplicated, Rearranged, and Weakly Expressed in High Oleic Acid Sunflower Lines, The Plant Genome, Crop Science Society of America, vol. 38, No. 5, pp. 1245-1249 (1998).
Lacombe et al., Genetic, molecular and expression features of the Pervenets mutant leading to high oleic acid content of seed oil in sunflower, O.C.L. Oleagineux Corps Gras Lipides, Editions John Libbey Eurotext, Montrouge, FR, vol. 9, No. 1, pp. 17-23 (2002).

\* cited by examiner

*Primary Examiner* — Ashley K Buran
*Assistant Examiner* — Wayne Zhong
(74) *Attorney, Agent, or Firm* — Mandar A. Joshi; Bret E. Field; Bozicevic, Field & Francis LLP

(57) ABSTRACT

Isolated nucleotide sequences mutated by insertion encoding a truncated sunflower oleate desaturase protein, truncated protein, methods, procedures and uses. The isolated nucleotide sequences comprise an insertion that includes a stop codon, and wherein the sequences encode a truncated sunflower oleate desaturase protein. The truncated sunflower oleate desaturase protein may be for example the sequence shown in SEQ ID No: 1 or SEQ ID No: 2.

14 Claims, 1 Drawing Sheet
Specification includes a Sequence Listing.

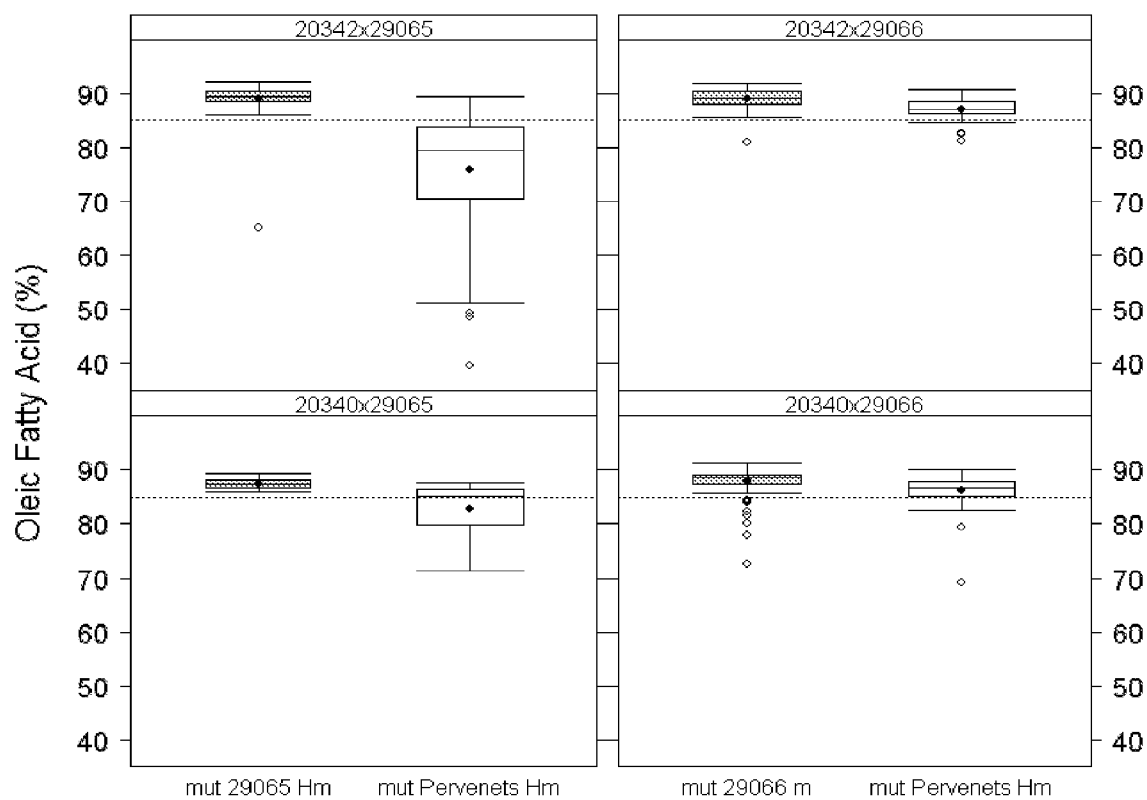

SEQUENCE LISTING

<160> NUMBER OF SEQ ID NOS: 28

<210> SEQ ID NO 1
<211> LENGTH: 104
<212> TYPE: PRT
<213> ORGANISM: Helianthus annuus

<400> SEQUENCE: 1

Met Gly Ala Gly Glu Tyr Thr Ser Val Thr Asn Glu Asn Asn Pro Leu
1               5                   10                  15

Asp Arg Val Pro His Ala Lys Pro Pro Phe Thr Ile Gly Asp Leu Lys
            20                  25                  30

Lys Ala Ile Pro Pro His Cys Phe Gln Arg Ser Leu Thr Arg Ser Phe
        35                  40                  45

Ser Tyr Val Leu Ser Asp Leu Thr Ile Thr Ala Val Leu Tyr His Ile
    50                  55                  60

```
Ala Thr Thr Tyr Phe His His Leu Pro Thr Pro Leu Ser Ser Ile Ala
 65                  70                  75                  80

Trp Ala Ser Tyr Trp Val Val Gln Gly Cys Val Leu Thr Gly Val Trp
                 85                  90                  95

Val Ile Ala His Glu Cys Gly Leu
            100
```

```
<210> SEQ ID NO 2
<211> LENGTH: 71
<212> TYPE: PRT
<213> ORGANISM: Helianthus annuus

<400> SEQUENCE: 2
```

```
Met Gly Ala Gly Glu Tyr Thr Ser Val Thr Asn Glu Asn Asn Pro Leu
 1               5                  10                  15

Asp Arg Val Pro His Ala Lys Pro Pro Phe Thr Ile Gly Asp Leu Lys
             20                  25                  30

Lys Ala Ile Pro Pro His Cys Phe Gln Arg Ser Leu Thr Arg Ser Phe
         35                  40                  45

Ser Tyr Val Leu Ser Asp Leu Thr Ile Thr Ala Val Leu Tyr His Ile
     50                  55                  60

Ala Thr Thr Cys Lys Phe Trp
 65                  70
```

```
<210> SEQ ID NO 3
<211> LENGTH: 1922
<212> TYPE: DNA
<213> ORGANISM: Helianthus annuus

<400> SEQUENCE: 3
atgggtgcag agaatacac gtctgtgacc aacgaaaaca acccactcga tcgagtccct    60
catgcaaaac caccttcac catcggcgat ctgaaaaaag ccatcccacc acactgcttc   120
cagcggtcgc taacccgttc gttctcctac gtgctgtctg acctcaccat aaccgctgtc   180
ctctaccaca ttgccaccac ctacttccac cacctcccca cccctttgtc atccatcgca   240
tgggcctctt actgggtagt ccaaggctgc gtcctcaccg gagtctgggt catcgcccac   300
gaatgtggtc tgtgaaaaat ggtatgaaca tccaatacaa aactcaaaga ataacataaa   360
acacaagaga agcgacaaaa acgtgacaga aaactttatt atttaaccca aaccgaaaaa   420
caccccccaa accctagatc tcaagaagat gagatctgtg taatacaatg aacaaataca   480
acagatcagt aagatctatt gactgagaaa acaaaataaa ccaaaaacat acacagagat   540
aacaagttct ttgaaacaca accgtgattt ctacaagaaa tcactaagac tatcggctga   600
gacaactccg gctggagaca gcaacaactg aagacaacag caacaattac tcagacaacg   660
gctgattaca gcgacaaata cgaacttgaa accctaatcg cctgtaaaga accagagaaa   720
gatgaaaata taattgtgag agagtaataa cttagaaaga attttggggg tgaacaagag   780
agaactgtgt gcgtaacaat tgaggattaa tcatagaaat atccagaacc tctcattta    840
tatcagttgt tgaataaatt acactttagt ccaagagata tgttgatgat gatcgcagtc   900
cccaaaagtt tcacaaacca ccctcagact tccagctatt ataaccaact cacgaacaaa   960
caataacaac cgtatatacc aatcagccta caataacaag cctaaagacg tatatccagc  1020
ccagtaaata aagagcccaa tcataacatg ttgcaacctg gatgacaacc caagcttgac  1080
atttttaaca tggtcaccat gcgtttagtg attatcaatg ggtcgacgac actgtgggct  1140
tgttctccca ctcgtcttta ctcgtccctt acttttcgtg gaatatagt caccaccgcc  1200
```

-continued

| | |
|---|---|
| accattccaa cactggatca ctcgagcggg acgaggtttt cgtccccaaa tcccgatcga | 1260 |
| aagtcccgtg gtactcgaaa tactttaaca acacagtggg ccgcattgtc agtatgttcg | 1320 |
| tcactctcac tctcggctgg cccttgtact tagctttcaa tgtgtcgggc cgaccctatg | 1380 |
| accgtttcgc ctgccactac gtcccaacca gccctatgta caatgaacgt aaacgttacc | 1440 |
| agatagtcat gtccgacatc gggattgtta tcacatcgtt catcctttat cgtgttgcta | 1500 |
| tggcaaaagg gttggtttgg gtgatttgcg tctatggggt tccgttgatg gttgtgaacg | 1560 |
| cgtttctggt gttgatcact tatcttcaac atactcaccc tggcttgccg cattatgata | 1620 |
| gctcggaatg ggaatggtta aagggagcat tggcgacagt ggaccgtgac tatggtgtgt | 1680 |
| tgaacaaggt gttccatcat attaccgaca cacatgtggt gcaccatttg ttttcgacaa | 1740 |
| tgcctcatta taatgcgatg gaagcacaga aggcgctgag accggtgctt ggggagtatt | 1800 |
| atcggtttga caagaccccg ttttatgtag ccatgtggag agagatgaag gaatgtttgt | 1860 |
| ttgtggagca agatgatgaa gggaaaggag gtgtgttttg gtacaagaat aagatgaatt | 1920 |
| aa | 1922 |

<210> SEQ ID NO 4
<211> LENGTH: 6009
<212> TYPE: DNA
<213> ORGANISM: Helianthus annuus
<220> FEATURE:
<221> NAME/KEY: misc_feature
<222> LOCATION: (4156)..(4156)
<223> OTHER INFORMATION: n is a, c, g, or t

<400> SEQUENCE: 4

| | |
|---|---|
| atgggtgcag gagaatacac gtctgtgacc aacgaaaaca acccactcga tcgagtccct | 60 |
| catgcaaaac caccctthcac catcggcgat ctgaaaaaag ccatcccacc acactgcttc | 120 |
| cagcggtcgc taacccgttc gttctcctac gtgctgtctg acctcaccat aaccgctgtc | 180 |
| ctctaccaca ttgccaccac ctgtaaattt tggtaatcag agagactaat tgcttttgtt | 240 |
| ttctatttat catcacacaga accacacatc aaaatcgaat acatatgaca cagcaaagag | 300 |
| aaaaaaatgg aactaaccct aacaagataa gtctaaactt agataaggct aattcaaata | 360 |
| aaacaattaa aaaataacta aacgtggcca gcaaataact ccaatattcc ccctcaagtt | 420 |
| ggagcgtgca atcttgcat ccccaacttg acaagtaagc ttcgaaggtg ttgagctccc | 480 |
| aacggtttgg ttagcagatc agctattkgc atctttgaat cgatatgaag aggaaggatt | 540 |
| tcttttgact ctacgcgttc tcgaacaaag aaacaatcca tctccacatg tttggttctt | 600 |
| tcatggaaaa cagggttatt ggcaatgtgc ttcgctgcca agttgtcaca aaatagcacg | 660 |
| gttccatcat tttggggttc atcgagttct gccaacaaag cacgcaccca caaaacttca | 720 |
| ctgactgtgg atgccattgc cctgttattc agcttctgca gatgagcgag atactactga | 780 |
| ctgcttcttt gacttccatg aaataggcgc tcctccaagc aacaacaagt aacctgtacg | 840 |
| agtagcgcct ggttgaaggg caacctaacc aatctgcatc acagtatgac actaacctcg | 900 |
| tccctccttc cttttgcaac aagattcctt gccctggag ccgccttcaa gtagcggagc | 960 |
| acccgaaccg cggcatccaa atggttttgt cgtgggctct ccacgaattg gctaaggaca | 1020 |
| tttacggaat aagtaatgtc tggtcgtgtt gcctgtaggt acaacaatct tccaaccagt | 1080 |
| ctcctgtact tgttggcatc aacctttttgt tcctcttccc ctttatcaag ctttagagtt | 1140 |
| tgttccatag gaaacccgct cggacgacat ccagtgagac cacaatcctc caaaatatcg | 1200 |
| agcgtatatt ttctttggct aagaaccaaa ccaccttttg ttcgtgccac ttcgatgcct | 1260 |

-continued

```
aaaaagtatt ttaatggacc caagtctttg atgctgaact gatcatgaag ttgagatttt    1320
acaaaacgaa tcatctcgtt attattgcct accacgatga cgtcatccac gtaaattaaa    1380
gccgctacat acgtctcgcc ccttttgtaa atgaacaatg aataatcggc ttttgattga    1440
gaaaaaccca atgctaacaa cgcttttgta aatttgtggt accagttgcg cgaggcttgc    1500
ttgagaccgt atattgactt tctaaggcgg cacactcgag tctcggtctc tttcgaaaac    1560
ccttgcggaa gcttcatata cacctcttct tcgaggtcac catgtaagaa cgcgttgttg    1620
acatcaagtt ggtgtatgat ccagtctctt tttacggcta aagtgagtag agacctcaca    1680
gtgaccagct ttgcaactgg agcaaacgtg tcatggtagt caactccctc caactgtgtg    1740
aaccccttttg caaccagtct ggctttgtac ctttcgactt gaccatttgg cttgtattta    1800
actttgtata cccatttgga atcaatcgct ttctttcctt cgggcaactt ttcaagtgtc    1860
caggttccat ttcgttccaa ggcctttatt tcgttttttca ttgcctctcg ccacctgtca    1920
tcctgtgtaa gcttcgtaaa aattttttcgg ctcatcatgt gacgtgatgg ccgcaagaaa    1980
agctttatgg ttatttgaaa atttgtcata aggagatgta attggcaaga ggatgtaccg    2040
tagaggagcc ttgatcggag tccgggtgtg catggttgac tgacgggggg agctttacgt    2100
ggtagtcttt aaaccgagct ggcggaactc gtgatcgttg cgaggtgcgc aacattgggc    2160
tcgttggttg ttcttggggc tcggtcctgg atgggctcgc atcttcaact gacccatgtg    2220
tctcaacttg ttcttcgtca ttgttaggcc cactgttttc ggcattttca gattgtattg    2280
gcccaatatc atcatcactt tcaagatcaa tttcgattgg gcccaactct atattttcaa    2340
gaaaatcacc tcccaactca tttctttggc cactgttcac gtgggtatta tcatgaccaa    2400
ctttgtgatt tgttggaac tcatttaata tttcttcatc tccactatga cttgaaagtt    2460
tggtttcggt tgaaacggg aatgtttctt caacgaactt aacatcccga ctaacaataa    2520
ttttctttct ttccaaatca tagattttgt acccttttcgt cccaaaagga tatccaagaa    2580
acacccctgc ttttcctctt ggagcgaact tatccccgat tcgtttcggt attccaaaaa    2640
tacgttaagc acccaaaaac ccgcatgtgg tcataaacag gttgtcgttt aaaaatgact    2700
tcatacgggg ttttgtattt gaggactttt gacggtaacc tattgatgat ataggcggcc    2760
gtcaagacac attccccca aaaccttatt ggtaagttgg cttcgaaacg aagtgcccgt    2820
gcaatctcta gaaggtgtcg gtgctttctc tctactaccc catttttgttg tggggtgtgc    2880
gggcaagtcg tttcgagttc aatgccccga tcactgtaaa atgtttttcat gcgatttgag    2940
gtgaactcac cccccgttgt cgcatctgat tcgtttgaca ctcttcttgt attgcgtttg    3000
gattagattg caaaaactga ccaaaaaatc actcgcttca tttttatgcc ttattatata    3060
aacccaaacg gcccgactaa aatcatcaac tatggtgaga aaataactgc cacgagtgag    3120
tgaaaacgtt cgataaccac cccaaatgtc acagtgtatc atgtcaaaac aatcactagt    3180
ttttattgaa cttgttttgaa atggcaatct agtcatttta gctttgacac acgaatcaca    3240
aaaggaaggt ttcgaatcat tactagaaat gtttaaaaca tgaatacgtg acattttatc    3300
atttgatggg tgtccaagtc ttctatgcca gttacttgaa gtcgttgcag ccatagctct    3360
tcgatctttt cgcatggctc ccatcctata aagtccccct ctgcacttac ccgttccaaa    3420
tcaagttcct gtcctcaggc cctgtatgac aaagaaatca ggaaaaaacg tgacagcaca    3480
ctgtaagtct ctcgttaggc ggctaatgga caaaaggttg catttaaaat taggcacaaa    3540
aagaactcct ttaattttaa ccctcctttt gaacaaatgt tgcccgttc ccttaaacag    3600
ggacaacgtc cccattagga attgtaacag gtgtctcatc attgttcaag gagagttttt    3660
```

-continued

```
caagaaactc ccgaacacat gtcatgtatt cggtggctcc cgtatccaga atccactcac    3720
catcctcatt gattctacct gccatgtttg ccctcgggtt gtcattggtt ttgttttgat    3780
catcatgttt accaaacagc tttgtaaaca tctcatactg ttcatccgtt aatccaggta    3840
ttttgcttgc ggtggactcg acaagggcgg cttcggctt tgcggcttcc ttctttgtct     3900
tcccgggcca ccattccgga tatcccacca gtttaaaaca cccttcacga acatgtccat    3960
cccgtccgca atgtgtgcaa tgacccgtct ggtaagtgtc gtgggcctgt cagcatttag    4020
cccaagtttt cttttgggcc tgtggatcac gattagcagg ctgccaagct tgaaaggctg    4080
cggcttccgg cccagcgaca gttttcttcc cggttgcgat ggcccgctgc cttcgtcttt    4140
ctgctacgaa gtgatnggct ctcctaggg acggcatggt tttcgtggcg agaatctgag     4200
tgcgcatgac agaaaattct gcatctaacc ccattaaaaa ttcataaagc cgctccttt     4260
ctttaagatc cgtgattttc ttcccgactt cgcatttaca aagtccacag tcgcacgttg    4320
ggagtgggaa gcaccgaatc caactcgtcc cacaaagcgc gcagcttggt gaaataagcc    4380
gaaacggacg aaccctcttg acgcgtagtg gtaattgact gtttcaactc gtatgttctc    4440
tggggcgctt tcttttccaa aacgttcatg cagatcgttc cagatttcca gcgccgtatt    4500
tgcgtacttc acactgttgc gtatttcctt ctccatggcg gtagttaacc acccttttat    4560
catggcgtca cagcgcatcc actgcttgta acgcttatca gttttgtcgg gtttgggaag    4620
ggttccatca acgaactcta tcttgttttt ggcaaaaagg aaattcgtca tctcttgaat    4680
ccaatccttg aaattgccat cggtgagagt ttcgtttacg tggagagttt ttggatagtc    4740
tgacggatgc aagtagcagg gcgaattcac gtcaggagca tcaccgccgc cggaagaacc    4800
aggttgttct ccggccatga tcttcttgct attgatgatt ttaatgatga acgatctgct    4860
ctgataccat gtaaattttg gtcaatcaga gagactaatt gcttttgttt tctatttatt    4920
catacacaga accacacatc aaaatcgaat acatatacac agcaaagaga aaaaatgga    4980
actaacccta acaagataag tctaaactta gataaggcta attcaaataa aacaattaaa    5040
aaataactaa acgtggccag caaataactc caatacttcc accacctccc caccccttg     5100
tcatccatcg catgggcctc ttactgggta gtccaaggct gcgtcctcac cggagtctgg    5160
gtcatcgccc acgaatgtgg tcaccatgcg tttagtgatt atcaatgggt cgacgacact    5220
gtgggctttg ttctccactc gtctttactc gtcccttact tttcgtggaa atatagtcac    5280
caccgccacc attccaacac tggatcactc gagcgggacg aggttttcgt ccccaaatcc    5340
cgatcgaaag tcccgtggta ctcgaaatac tttaacaaca cagtgggccg cattgtcagt    5400
atgttcgtca ctctcactct cggctggccc ttgtacttag ctttcaatgt gtcgggccga    5460
ccctatgacc gtttcgcctg ccactacgtc ccaaccagcc ctatgtacaa tgaacgtaaa    5520
cgttaccaga tagtcatgtc cgacatcggg attgttatca catcgttcat cctttatcgt    5580
gttgctatgg caaaagggtt ggtttgggtg atttgcgtct atggggttcc gttgatggtt    5640
gtgaacgcgt ttctggtgtt gatcacttat cttcaacata ctcaccctgg cttgccgcat    5700
tatgatagct cggaatggga atggttaaag ggagcattgg cgacagtgga ccgtgactat    5760
ggtgtgttga acaaggtgtt ccatcatatt accgacacac atgtggtgca ccatttgttt    5820
tcgacaatgc ctcattataa tgcgatggaa gcacagaagg cgctgagacc ggtgcttggg    5880
gagtattatc ggtttgacaa gacccgtttt tatgtagcca tgtggagaga gatgaaggaa    5940
tgtttgtttg tggagcaaga tgatgaaggg aaaggaggtg tgttttggta caagaataag    6000
atgaattaa                                                           6009
```

<210> SEQ ID NO 5
<211> LENGTH: 1137
<212> TYPE: DNA
<213> ORGANISM: Helianthus annuus

<400> SEQUENCE: 5

```
atgggtgcag gagaatacac gtctgtgacc aacgaaaaca acccactcga tcgagtccct        60
catgcaaaac caccctttcac catcggcgat ctgaaaaaag ccatcccacc acactgcttc      120
cagcggtcgc taacccgttc gttctcctac gtgctgtctg acctcaccat aaccgctgtc      180
ctctaccaca ttgccaccac ctacttccac cacctcccca cccctttgtc atccatcgca      240
tgggcctctt actgggtagt ccaaggctgc gtcctcaccg gagtctgggt catcgcccac      300
gaatgtggtc accatgcgtt tagtgattat caatgggtcg acgacactgt gggctttgtt      360
ctccactcgt ctttactcgt cccttacttt tcgtggaaat atagtcacca ccgccaccat      420
tccaacactg gatcactcga gcgggacgag gttttcgtcc caaatcccg atcgaaagtc       480
ccgtggtact cgaaatactt taacaacaca gtgggccgca ttgtcagtat gttcgtcact      540
ctcactctcg gctggccctt gtacttagct ttcaatgtgt cgggccgacc ctatgaccgt      600
ttcgcctgcc actacgtccc aaccagccct atgtacaatg aacgtaaacg ttaccagata      660
gtcatgtccg acatcgggat tgttatcaca tcgttcatcc tttatcgtgt tgctatggca      720
aaagggttgg tttgggtgat tgcgtctat ggggttccgt tgatggttgt gaacgcgttt       780
ctggtgttga tcacttatct tcaacatact caccctggct gccgcatta tgatagctcg       840
gaatgggaat ggttaaaggg agcattggcg acagtggacc gtgactatgg tgtgttgaac      900
aaggtgttcc atcatattac cgacacacat gtggtgcacc atttgttttc gacaatgcct      960
cattataatg cgatggaagc acagaaggcg ctgagaccgg tgcttgggga gtattatcgg     1020
tttgacaaga ccccgtttta tgtagccatg tggagagaga tgaaggaatg tttgtttgtg     1080
gagcaagatg atgaagggaa aggaggtgtg ttttggtaca agaataagat gaattaa        1137
```

<210> SEQ ID NO 6
<211> LENGTH: 378
<212> TYPE: PRT
<213> ORGANISM: Helianthus annuus

<400> SEQUENCE: 6

```
Met Gly Ala Gly Glu Tyr Thr Ser Val Thr Asn Glu Asn Asn Pro Leu
1               5                   10                  15

Asp Arg Val Pro His Ala Lys Pro Pro Phe Thr Ile Gly Asp Leu Lys
            20                  25                  30

Lys Ala Ile Pro Pro His Cys Phe Gln Arg Ser Leu Thr Arg Ser Phe
        35                  40                  45

Ser Tyr Val Leu Ser Asp Leu Thr Ile Thr Ala Val Leu Tyr His Ile
    50                  55                  60

Ala Thr Thr Tyr Phe His His Leu Pro Thr Pro Leu Ser Ser Ile Ala
65                  70                  75                  80

Trp Ala Ser Tyr Trp Val Val Gln Gly Cys Val Leu Thr Gly Val Trp
                85                  90                  95

Val Ile Ala His Glu Cys Gly His His Ala Phe Ser Asp Tyr Gln Trp
            100                 105                 110

Val Asp Asp Thr Val Gly Phe Val Leu His Ser Ser Leu Leu Val Pro
        115                 120                 125

Tyr Phe Ser Trp Lys Tyr Ser His Arg His His Ser Asn Thr Gly
    130                 135                 140
```

Ser Leu Glu Arg Asp Glu Val Phe Val Pro Lys Ser Arg Ser Lys Val
145                 150                 155                 160

Pro Trp Tyr Ser Lys Tyr Phe Asn Asn Thr Val Gly Arg Ile Val Ser
                165                 170                 175

Met Phe Val Thr Leu Thr Leu Gly Trp Pro Leu Tyr Leu Ala Phe Asn
            180                 185                 190

Val Ser Gly Arg Pro Tyr Asp Arg Phe Ala Cys His Tyr Val Pro Thr
        195                 200                 205

Ser Pro Met Tyr Asn Glu Arg Lys Arg Tyr Gln Ile Val Met Ser Asp
    210                 215                 220

Ile Gly Ile Val Ile Thr Ser Phe Ile Leu Tyr Arg Val Ala Met Ala
225                 230                 235                 240

Lys Gly Leu Val Trp Val Ile Cys Val Tyr Gly Val Pro Leu Met Val
                245                 250                 255

Val Asn Ala Phe Leu Val Leu Ile Thr Tyr Leu Gln His Thr His Pro
            260                 265                 270

Gly Leu Pro His Tyr Asp Ser Ser Glu Trp Glu Trp Leu Lys Gly Ala
        275                 280                 285

Leu Ala Thr Val Asp Arg Asp Tyr Gly Val Leu Asn Lys Val Phe His
    290                 295                 300

His Ile Thr Asp Thr His Val Val His His Leu Phe Ser Thr Met Pro
305                 310                 315                 320

His Tyr Asn Ala Met Glu Ala Gln Lys Ala Leu Arg Pro Val Leu Gly
                325                 330                 335

Glu Tyr Tyr Arg Phe Asp Lys Thr Pro Phe Tyr Val Ala Met Trp Arg
            340                 345                 350

Glu Met Lys Glu Cys Leu Phe Val Glu Gln Asp Asp Glu Gly Lys Gly
        355                 360                 365

Gly Val Phe Trp Tyr Lys Asn Lys Met Asn
    370                 375

<210> SEQ ID NO 7
<211> LENGTH: 26
<212> TYPE: DNA
<213> ORGANISM: Artificial Sequence
<220> FEATURE:
<223> OTHER INFORMATION: primer OLD1-F2

<400> SEQUENCE: 7
gaaaagtctg gtcaaacagt caacat                                          26

<210> SEQ ID NO 8
<211> LENGTH: 21
<212> TYPE: DNA
<213> ORGANISM: Artificial Sequence
<220> FEATURE:
<223> OTHER INFORMATION: primer OLD1-R2

<400> SEQUENCE: 8
ccgatgtcgg acatgactat c                                               21

<210> SEQ ID NO 9
<211> LENGTH: 24
<212> TYPE: DNA
<213> ORGANISM: Artificial Sequence
<220> FEATURE:
<223> OTHER INFORMATION: primer OLD1adv-F2

```
<400> SEQUENCE: 9
aaatacttta acaacacagt gggc                                    24

<210> SEQ ID NO 10
<211> LENGTH: 26
<212> TYPE: DNA
<213> ORGANISM: Artificial Sequence
<220> FEATURE:
<223> OTHER INFORMATION: primer OLD1-R3

<400> SEQUENCE: 10
ccagaaccag dacaacagcc attgtc                                  26

<210> SEQ ID NO 11
<211> LENGTH: 21
<212> TYPE: DNA
<213> ORGANISM: Artificial Sequence
<220> FEATURE:
<223> OTHER INFORMATION: primer OLD1-Walk3'-F1

<400> SEQUENCE: 11
aaccaccctt caccatcggc g                                       21

<210> SEQ ID NO 12
<211> LENGTH: 20
<212> TYPE: DNA
<213> ORGANISM: Artificial Sequence
<220> FEATURE:
<223> OTHER INFORMATION: primer OLD1-Walk3'-F2

<400> SEQUENCE: 12
acccgttcgt tctcctacgt                                         20

<210> SEQ ID NO 13
<211> LENGTH: 20
<212> TYPE: DNA
<213> ORGANISM: Artificial Sequence
<220> FEATURE:
<223> OTHER INFORMATION: primer OLD1-Walk5'-R1

<400> SEQUENCE: 13
agtggcaggc gaaacggtca                                         20

<210> SEQ ID NO 14
<211> LENGTH: 20
<212> TYPE: DNA
<213> ORGANISM: Artificial Sequence
<220> FEATURE:
<223> OTHER INFORMATION: primer OLD1-Walk5'-R2

<400> SEQUENCE: 14
agccgagagt gagagtgacg                                         20

<210> SEQ ID NO 15
<211> LENGTH: 20
<212> TYPE: DNA
<213> ORGANISM: Artificial Sequence
<220> FEATURE:
<223> OTHER INFORMATION: primer MUT29010HO-W2-5'-1

<400> SEQUENCE: 15
atgatcgcag tccccaaaag                                         20
```

```
<210> SEQ ID NO 16
<211> LENGTH: 21
<212> TYPE: DNA
<213> ORGANISM: Artificial Sequence
<220> FEATURE:
<223> OTHER INFORMATION: primer MUT29010HO-W2-5'-2

<400> SEQUENCE: 16
ccaatcagcc tacaataaca a                                              21

<210> SEQ ID NO 17
<211> LENGTH: 20
<212> TYPE: DNA
<213> ORGANISM: Artificial Sequence
<220> FEATURE:
<223> OTHER INFORMATION: primer MUT29010HO-W2-3'-1

<400> SEQUENCE: 17
aagggacgag taaagacgag                                                20

<210> SEQ ID NO 18
<211> LENGTH: 20
<212> TYPE: DNA
<213> ORGANISM: Artificial Sequence
<220> FEATURE:
<223> OTHER INFORMATION: primer MUT29010HO-W2-3'-2

<400> SEQUENCE: 18
tcgtcgaccc attgataatc                                                20

<210> SEQ ID NO 19
<211> LENGTH: 20
<212> TYPE: DNA
<213> ORGANISM: Artificial Sequence
<220> FEATURE:
<223> OTHER INFORMATION: primer MUTHA89HO-W2-5'-1

<400> SEQUENCE: 19
ggaaaacagg gttattggca                                                20

<210> SEQ ID NO 20
<211> LENGTH: 20
<212> TYPE: DNA
<213> ORGANISM: Artificial Sequence
<220> FEATURE:
<223> OTHER INFORMATION: primer MUTHA89HO-W2-5'-2

<400> SEQUENCE: 20
caacaaagca cgcacccaca                                                20

<210> SEQ ID NO 21
<211> LENGTH: 20
<212> TYPE: DNA
<213> ORGANISM: Artificial Sequence
<220> FEATURE:
<223> OTHER INFORMATION: primer MUTHA89HO-W52-1

<400> SEQUENCE: 21
tcatggtagt caactccctc                                                20

<210> SEQ ID NO 22
<211> LENGTH: 21
<212> TYPE: DNA
<213> ORGANISM: Artificial Sequence
<220> FEATURE:
<223> OTHER INFORMATION: primer MUTHA89HO-W52-2
```

```
<400> SEQUENCE: 22
cgctttcttt ccttcgggca a                                              21

<210> SEQ ID NO 23
<211> LENGTH: 20
<212> TYPE: DNA
<213> ORGANISM: Artificial Sequence
<220> FEATURE:
<223> OTHER INFORMATION: primer MUTHA89HO-W32-1

<400> SEQUENCE: 23
gctaatcgtg atccacaggc                                                20

<210> SEQ ID NO 24
<211> LENGTH: 19
<212> TYPE: DNA
<213> ORGANISM: Artificial Sequence
<220> FEATURE:
<223> OTHER INFORMATION: primer MUTHA89HO-W32-2

<400> SEQUENCE: 24
gcccacgaca cttaccaga                                                 19

<210> SEQ ID NO 25
<211> LENGTH: 20
<212> TYPE: DNA
<213> ORGANISM: Artificial Sequence
<220> FEATURE:
<223> OTHER INFORMATION: primer MUTHA89HO-W53-1

<400> SEQUENCE: 25
cccaactcta tattttcaag                                                20

<210> SEQ ID NO 26
<211> LENGTH: 20
<212> TYPE: DNA
<213> ORGANISM: Artificial Sequence
<220> FEATURE:
<223> OTHER INFORMATION: primer MUTHA89HO-W53-2

<400> SEQUENCE: 26
acttgaaagt ttggtttcgg                                                20

<210> SEQ ID NO 27
<211> LENGTH: 20
<212> TYPE: DNA
<213> ORGANISM: Artificial Sequence
<220> FEATURE:
<223> OTHER INFORMATION: primer MUTHA89HO-W33-1

<400> SEQUENCE: 27
agggaacggg gcaacatttg                                                20

<210> SEQ ID NO 28
<211> LENGTH: 19
<212> TYPE: DNA
<213> ORGANISM: Artificial Sequence
<220> FEATURE:
<223> OTHER INFORMATION: primer MUTHA89HO-W33-2

<400> SEQUENCE: 28
gccgcctaac gagagactt                                                 19
```

NUCLEOTIDE SEQUENCES MUTATED BY INSERTION THAT ENCODE A TRUNCATED OLEATE DESATURASE PROTEIN, PROTEINS, METHODS AND USES

The present invention relates to isolated nucleotide sequences that encode a mutated oleate desaturase sunflower protein, to the mutated protein, to plants producing the protein, to seeds and oils produced by the plant, to methods for obtaining the mutated sequences and the plant, and to uses of the protein and the plant. desaturase desaturase

BACKGROUND

The oleate desaturase acid enzyme (OLD) is involved in the enzymatic conversion of oleic acid to linoleic acid. The microsomal OLD have been cloned and characterized using the marker technology by T-DNA (T-DNA tagging, Okuley, et al. (1994) *Plant Cell* 6:147-158). Nucleotide sequences of higher plants encoding microsomal OLD have been described in document WO94/11516 PCT of Lightner et al.

Sunflower is generally cultivated to obtain oils that contain saturated fatty acids (palmitic and stearic) and unsaturated fatty acids (oleic and linoleic). The stearic acid content is always lower than 10% (Guston et al. (1986) *The lipid handbook*, Chapman and Hall Great Britain), usually between 3 and 7%. In relation to the content of unsaturated fatty acids there are two types of sunflower seeds: the normal sunflower, which has a linoleic acid content between 50% to 70% (Knowles (1988) Recent advances in oil crops breeding, *AOCS Proceedings*) and sunflower with high oleic content, which has a linoleic acid content of 2% to 10% and oleic acid content from 75% to 90% (Soldatov (1976) *Chemical mutagenesis in sunflower breeding, Proceedings of the 7th International Sunflower Conference*, 352-357). There is also a sunflower line that has a high content of palmitic acid between 22 and 40% (Ivanov et al. (1988) *Sunflower Breeding for High Palmitic Acid Content in the Oil, Proceedings of the 12th International Sunflower Conference*, Vol II, 453-465) and another line of sunflower with low content of saturated fatty acids (less than 6%) (EP-A-0496504).

In order to respond to the need for vegetable oils of interest to both the industry and to human food consumption, efforts are made in improving varieties of oilseeds focused on modifying the fatty acid composition of seeds, for example, by means of conventional breeding programs, mutagenesis or transgenesis.

Mutations are typically induced with extremely high doses of radiation or chemical mutagens (Gaul (1964) *Radiation Botany* 4:155-232). High doses exceed the lethal dose 50% ($LD_{50}$), and generally lethal doses of 90% ($LD_{90}$) maximize the percentage of possible mutations.

Mutagenesis conducted by Soldatov in 1976 in a population of sunflower allowed obtaining the population of so-called Pervenets mutants. The average content of oleic fatty acid (18:1) of the seeds of this cultivar is higher than 65%, the individual content is between 60 and 80% while in normal varieties (low oleic, LO) this content is approximately 20%. The Pervenets population was distributed worldwide and used in many breeding programs in order to convert certain genotypes with low content of 18:1 into genotypes with a high content of 18:1 in their seed.

The accumulation of 18:1 in seeds is dependent on two enzymatic reactions: the desaturation of 18:0 (stearic acid) to 18:1 and the subsequent desaturation of 18:1 to 18:2 (linoleic acid). The oleate desaturase enzyme (OLD) catalyzes the desaturation of 18:1 to 18:2 (Ohlrogge and Browse (1995) *The Plant Cell,* 7:957-970, Somerville and Browse (1996) *Trends Cell Biol* 6:148-153; Schwartzbeck (2001) *Phytochemistry,* 57:643-652).

Sunflower oil is naturally rich in 18:2 (55-70%) and consequently poor in 18:1 (20-25%). Traditional varieties are classified as low oleic (LO). As there exists a high interest among consumers of eating more healthy oils with high oleic acid content, there is also an interest in developing high oleic sunflower plants, which preferably also lead to similar crop yields as the conventional sunflower varieties.

Studies carried out by Garces et al. in 1989 and 1991 (Garces et al. (1989) *Phytochemistry* 28:2597-2600; Garces and Mancha (1991) *Phytochemistry* 30:2127-2130) showed that the high oleic phenotype (high oleic, HO) is associated with a marked decrease in the activity of the OLD enzyme, which catalyzes the desaturation of 18:1 to 18:2 in HO seeds during critical stages of the synthesis of the lipidic reserves, which explains the accumulation of 18:1.

The Pervenets mutation has been shown to be associated with gene duplications within the OLD gene, leading to gene silencing. This decrease in transcription of OLD explains the decrease in the amount of enzyme and therefore the low OLD activity demonstrated (Hongtrakul et al. (1998) *Crop Sci* 38:1245-1249) consistently to the 18:1 accumulation in sunflower seeds. This finding led to the development of molecular markers characteristic of the mutation that can be used in breeding programs to facilitate the selection of HO genotypes (WO2005/106022; Lacombe et al. (2001) *Life Sci* 324:839-845).

Traditional sunflower oil with high content of 18:2 is considered a healthy vegetable oil that has a proper taste, and it has been considered first class quality oil in the world market due to its high percentage of polyunsaturated fatty acids. It is used as a salad oil, cooking oil, or for production of margarine.

By modifying the fatty acid profile of sunflower oil, new oil can be developed having higher oxidative stability compared to conventional oil. This oil should at least contain a level of 18:1 of 55% to 65% in relation to the total fatty acids. The benefit of this oil is its high oxidative stability after the extraction process and the stability of the flavor of fried products. Sunflower oil with a high concentration of 18:1 does not need to be hydrogenated to improve stability and does not form trans fatty acids.

BRIEF DESCRIPTION OF THE INVENTION

It is an object of this invention to provide an Isolated nucleotide sequence encoding a mutated oleate desaturase protein (OLD) having a lower enzyme activity. This lower enzyme activity when expressed in a plant, in particular a sunflower plant, causes an increase in the amount of oleic acid in the plant oil or seed oil as compared to existing plants.

The invention thus relates to an isolated nucleotide sequence comprising an insertion that changes the reading frame, which nucleotide sequence encodes a truncated sunflower OLD protein. In a preferred embodiment, the inserted nucleotide sequence comprises a premature stop codon and encodes a truncated sunflower oleate desaturase protein that comprises the amino acid sequence of SEQ ID No:1 or SEQ ID No:2. The coding sequence of the truncated oleate desaturase protein can be the nucleotide sequence shown in SEQ ID No:3 or SEQ ID No:4.

According to a further aspect thereof this invention provides a truncated sunflower oleate desaturase protein comprising no more than 110 amino acids of the N-terminal end. In a preferred embodiment the amino acid sequence consists of SEQ ID NO:1 or SEQ ID No:2.

According to another aspect this invention relates to a sunflower plant comprising two alleles of the OLD with an insertion encoding an OLD truncated protein. Each allele comprises a nucleotide sequence that has an insertion comprising a premature stop codon and wherein said sequence encodes an OLD truncated protein. In a preferred embodiment the nucleotide sequence is SEQ ID No:3 or SEQ ID No:4. The mutated plant produces seeds with an oleic acid content between 80% and 95% with respect to the total percentage of fatty acids of the seed.

In a further embodiment thereof, the invention relates to a sunflower plant capable of producing seed having an oleic acid content between 80 and 95% with respect to the total fatty acid content of the seed, which plant is obtainable by crossing a plant of line 29065 that has the accession number NCIMB 41733 or of line 29066 that has the accession number NCIMB 41734 with another plant and selecting in the F2 for plants that produce seed having an oleic acid content between 80 and 95% with respect to the total percentage of fatty acids of the seed.

The invention also provides sunflower seed which comprises two alleles of the OLD with an insertion encoding a truncated oleate desaturase protein. Each allele comprises a nucleotide sequence that has an insert comprising a premature stop codon and wherein the sequence encodes a truncated protein desaturase oleate. The nucleotide sequence may be the sequence shown in SEQ ID No:3 or SEQ ID No:4. The amino acid sequence of the oleate desaturase protein may be the sequence shown in SEQ ID No:1 or SEQ ID No:2. In a preferred embodiment the seed is of line 29065, a representative seed sample of which was deposited under the accession number NCIMB 41733 or of line 29066, a representative seed sample of which was deposited under the accession number NCIMB 41734.

According to another aspect of this invention a sunflower oil is provided, which has an oleic acid content between 80% and 95% with respect to the total fatty acid content of the oil, which oil is obtainable from or obtained from sunflower seed that comprises two OLD alleles which have an insertion and encode a truncated oleate desaturase protein. In a preferred embodiment the oil is obtained from the seeds of line 29065, a representative seed sample of which was deposited under the accession number NCIMB 41733 or line 29066, a representative seed sample of which was deposited under the accession number NCIMB 41734.

The present invention further provides the use of sunflower seed for oil extraction. In a preferred embodiment the seed is of line 29065, a representative seed sample of which was deposited under the accession number NCIMB 41733 or of line 29066, a representative seed sample of which was deposited under the accession number NCIMB 41734.

The invention further relates to progeny of the claimed seed, wherein said progeny comprises an insertion in the gene that encodes an oleate desaturase protein, in which such insertion leads to the synthesis of a truncated oleate desaturase protein.

The invention further relates to a method for obtaining a sunflower plant with high oleic acid content which comprises the following steps:
 a) mutagenesis of part of a sunflower plant;
 b) obtaining at least one progeny of the mutant plant, and
 c) identifying and selecting at least one plant obtained in step b) comprising a nucleotide sequence that has an insertion that comprises a premature stop codon, and wherein said nucleotide sequence encodes a truncated oleate desaturase protein. In one embodiment the truncated oleate desaturase protein comprises a sequence of no more than 110 amino acids of the N-terminal end of the sunflower oleate desaturase, for example, the protein shown in SEQ ID No:1 or SEQ ID No:2.

According to another aspect thereof the invention provides a method for obtaining high oleic sunflower oil comprising extracting oil from seeds, a representative seed sample of which was deposited under accession number NCIMB 41733 or NCIMB 41734.

DESCRIPTION OF THE FIGURES

FIG. 1 displays a graph with the percentage of oleic acid in relation to all major fatty acids for homozygous plants for the high oleic Pervenets mutation, for lines 29065 and 29066 obtained in crosses 20342×29065; 20342×29066; 20340×29065 and 20340×29066. In all cases the percentages of oleic acid in F2 plants carrying mutations of the present invention in homozygous state (mut 29065 Hm and mut 29066 Hm, respectively) are compared with F2 plants carrying Pervenets mutation in homozygous state (mut Pervenets Hm). The points represent the mean and the segments within the boxes represent the medians.

DETAILED DESCRIPTION OF THE INVENTION

The present invention relates to mutated nucleotide sequences encoding an oleate desaturase that have an insertion, where the inserted sequence comprises a premature stop codon and therefore the sunflower oleate desaturase protein is truncated. The truncated oleate desaturase protein encoded has a lower enzyme activity leading to the plant or plant parts, such as seeds, to accumulate a large amount of oleic acid.

The truncated amino acid sequence can be any sequence that comprises no more than the first 110 amino acids of the N-terminal end of the sunflower oleate desaturase protein. In a preferred embodiment the truncated amino acid sequence may be the sequence shown in SEQ ID No:1 or the sequence shown in SEQ ID No:2.

The nucleotide sequences mutated by an insertion comprise a premature stop codon that lead to the synthesis of a sunflower truncated OLD protein. It should be understood that any nucleotide sequence that encodes an oleate desaturase protein that comprises not more than the first 110 amino acids of the N-terminal end of the wild type sunflower OLD, for example, the one from line HA89, are within the scope of this invention.

The nucleotide sequences that comprise an insertion that has a premature stop codon, for example the sequences shown in SEQ ID No:3 and SEQ ID No:4 are within the scope of the present invention.

Different sunflower lines have been mutated, for example lines HA89 and 29010 to obtain plants that produce seeds with high oleic acid content. Selected mutations in the coding sequence of the sunflower oleate desaturase gene were mutations by insertion of sequences that comprised a premature stop codon, said nucleotide sequences encode truncated oleate desaturase proteins.

Mutant seeds of the invention were deposited under the Budapest Treaty in the National Library of Industry, Food and Marine Bacteria (NCIMB) collection on Jul. 20, 2010 with the following accession numbers: line 29065 is accession number NCIMB 41733 and line 29066 is accession number NCIMB 41734.

The present invention relates to all seeds and plants, in particular sunflower seeds and plants that carry in their genome a mutation that leads to production of a truncated oleate desaturase protein having an enzyme activity that is lowered as compared to existing oleate desaturase enzymes leading to a higher oleic acid content in the seed oil. In one embodiment, the mutation is an insertion that carries a stop codon. Other mutations that lead to a truncation of the oleate desaturase to a maximum of 110 amino acids are also within the scope of this invention. Such plants and seeds that have a higher oleic acid content in the oil can be obtained by crossing with plants of the deposited lines 29065 (NCIMB 41733) or 29066 (NCIMB 41734) and selecting for progeny plants that have the higher oleic acid content. Selection is suitably made in the F2 since the mutation leading to the truncation must preferably be present homozygously for the lower enzyme activity to lead to the higher oleic acid content. Alternatively, the mutated gene can be brought into a sunflower plant by means of genetic engineering, in particular cisgenesis, with the mutant oleic desaturase gene described herein or any other gene leading to the same truncated expression product of not more than 110 amino acids.

Mutated plants and seeds of the invention can be obtained using different mutagenesis schemes. In a preferred embodiment a mutagenic agent such as EMS in a concentration between 5 and 15% is injected into the flower heads of the plants, the seeds are harvested and then X-ray radiation is applied.

Following mutagenesis, the fatty acid profile of mutated M2 seeds and parental seeds was analyzed, and those that showed a high content of oleic acid were selected, for example over 80% compared to the fatty acid content of seed, preferably about 90% compared to the total fatty acid content of the seed.

In another preferred embodiment, mutated plants and seeds were obtained by X-ray application. Subsequently, the fatty acid profile of M2 seeds was compared to the fatty acid profile of the parental seeds and those that showed a high content of oleic acid, for example having over 80% with respect to the total fatty acid content of the seeds, preferably about 90% compared to the total fatty acid content of the seed were selected.

The oil produced from any of the sunflower seeds of the invention has an oleic acid content higher than 80% with respect to the total fatty acid content of the seed, preferably higher than 85% and more preferably higher than 90%.

Directed crosses were performed between lines that belong to Advanta Semillas with high oleic phenotype, which are carriers of Pervenets mutation (20342 and 20340), and the high oleic mutants 29065 and 29066 of the invention: 20342×29065; 2042×29066; 20340×29065 and 20340×29066. F1 plants obtained in each cross were self-pollinated and their seeds (F2) were harvested. F2 seeds from each cross were planted in the field at Balcarce during the 2008/2009 season.

By means of using specific molecular markers, homozygous plants were identified for the Pervenets mutation and homozygous for mutations 29065 and 29066, obtained in each of the crosses. Said plants were self-pollinated and seeds were harvested individually. A group of 30 seeds was taken from each plant, grounded in a block and the fatty acid composition of oil was determined by gas chromatography.

In all cases, homozygous plants for mutations 29065 and 29066 showed average percentages of oleic acid higher than their corresponding counterparts with Pervenets mutation (see Table 3 and FIG. 1).

The nucleotide and amino acids sequences were compared with the corresponding sequences of the sunflower wild type line HA89 (SEQ ID No:5 and SEQ ID No:6). These sequences were identical to the corresponding ones of 29010 wild-type sunflower line.

The invention is illustrated by the following examples which should not be interpreted as limiting the scope thereof. On the contrary, it should be clearly understood that it is possible for those skilled in the field after reading the present disclosure to resort to other embodiments, modifications and equivalents of the invention, without deviating from the spirit of the present invention and/or scope of appended claims.

EXAMPLES

Example 1

1.1 Mutagenesis by X-Ray Irradiation (Generation of Line 29065)

M0 seeds of line 29010, proprietary of Advanta Semillas SAIC, were mutagenised by application of X-ray. Irradiation was carried out at the Institute of Genetics "Edward A. Favret", CICVyA-CNIA, INTA-Castelar, Argentina. The device for X-ray emission was a Philips MG 160, 4 KW with a maximum output of 160 KV, 19 mA and power use of 120 KV, 15 mA. The exposure time and dose used were 7 min 55 sec and 144 Grays, respectively, with a distance between the focus of the source and the object (seeds) of 40 centimeters.

The irradiated seeds were sown on Dec. 12, 2005, in 12 rows 100 meters long in Balcarce with lot number CA05-6347. The flower heads of the 1606 plants obtained were bagged before flowering in order to produce seeds by self-pollination, M2. The flower heads in each row were harvested and threshed individually. The M2 seeds of the 1606 plants were analyzed by gas chromatography (GC) to determine the fatty acid composition in 30 individual M2 seeds per plant. The mutant plant CA05-6347-725 showed a phenotype with a high content of oleic and was called 29065.

1.2 Mutagenesis by EMS Injection and Subsequent Irradiation with X Rays (Generation of Line 29066)

Seventy-five rows of seeds of line HA89 were sown in the Biotechnology Research Center of Advanta Semillas SAIC in Balcarce (Buenos Aires, Argentina) in the season 2004/5 and were identified under the lot number CA04-3, and 40 rows under the batch number CA04-1501. Each row was 6 meters long.

The flower heads of the plants were mutagenized by EMS injection (methanesulfonic acid ethyl ester) in doses of 5, 10 and 15% using a suitable mutagenesis protocol. Each M0 plant was bagged before flowering in order to produce self-pollinated M1 seeds. The flower heads of the plants of each EMS treatment were harvested, threshed and stored. The flower heads of the plants were mutagenized by injection with EMS (methanesulfonic acid ethyl ester) in doses of 5, 10 and 15% using the protocol described in WO2006/024351, and WO2008/071715. EMS is a mutagenic agent that induces transitions G/C to A/T (Jander et al. (2003) *Plant Physiol.* 131:139-146). In order to produce self-pollinated M1 seeds, each M0 plant was covered with a nylon mesh bag before flowering. The flower heads of the plants of each 5% EMS treatment were harvested, threshed and identified (lot CA04-3).

Said M1 seeds were subsequently mutagenized by X-ray application. Irradiation was carried out at the Institute of Genetics "Edward A. Favret", CICVyA-CNIA, INTA-Castelar, Argentina. The X-ray emission device was a Philips MG 160, 4 KW with a maximum output of 160 KV, 19 mA and power use of 120 KV, 15 mA. The exposure time and dose used were 7 min 55 sec and 144 Grays, respectively, with a distance between the source focus and the object (seeds) of 40 centimeters.

The irradiated seeds were sown on Dec. 12, 2005, in 16 rows of 100 meters long in Balcarce under the lot number CA05-6362. The flower heads of the 555 plants obtained were bagged before flowering in order to produce seeds by self-pollination, M2. The flower heads in each row were harvested and threshed individually. M2 seeds from 555 plants were analyzed by gas chromatography (GC) to determine the fatty acid composition in 30 individual M2 seeds per plant. The mutant plant CA05-6362-263 showed a phenotype with a high content of oleic and was called 29066.

Table 1 shows the mutagenesis method used for each mutant line of the invention, the nucleotide sequence and amino acid sequence of the truncated oleate desaturase protein.

TABLE 1

| Line | Mutagenesis Method | Size in base pairs of the insertion | Nucleotide position of the insertion in the OLD encoding region | Mutated nucleotide sequence of the invention | Sequence of the predicted OLD truncated protein |
|---|---|---|---|---|---|
| 29065 | X rays on seeds | 785 | 310 | SEQ ID N° 3 | SEQ ID N° 1 |
| 29066 | 5% EMS injection in the flower head followed by X rays on harvested seeds | 4872 | 201 | SEQ ID N° 4 | SEQ ID N° 2 |

Example 2

Analysis of the Fatty Acid Composition of the Seeds Oil by Gas Chromatography

Sunflower seeds are cut by the sagittal axis and placed in a 2 ml glass vial containing 0.25 ml of methylation solution consisting of methanol, toluene, dimethoxypropane and sulfuric acid in the ratio 66:28:4:2. The vials were capped and incubated for one hour at 80° C. They were allowed to cool at room temperature and then 1 ml of heptane was added (Garcés and Mancha (2003) *Analytical Biochemistry* 317: 247-254). The methyl esters of fatty acids present in the upper phase (heptane) were separated on a gas chromatograph Agilent 6890 with autosampler Model 7683B. The injector temperature was 240° C. and a capillary chromatographic column Durabond 15 meters in length, inner diameter of 250 µM and 250 µM film was used (J & W Scientific) at 200° C. $H_2$ gas was used as running gas at a pressure of 9.56 psi, flow 1.7 ml/min, and an average speed of 69 cm/sec. The methyl esters were detected with a flame ionization detector (FID) at 300° C. The results were integrated and analyzed using Chem32 Agilent Technologies software. The relative amounts of each fatty acid were measured in relation to a standard solution of methylated fatty acids (Alltech).

In Table 2 are shown the fatty acid composition analyses done by gas chromatography on seed samples from mutant plants from the invention.

TABLE 2

| | % of fatty acids | | | |
|---|---|---|---|---|
| Line | P | S | O | L |
| 29065 | 2.9 | 2.7 | 93.3 | 1.1 |
| 29066 | 4.4 | 3.7 | 90.6 | 1.3 |

P: palmitic acid;
S: stearic acid;
O: oleic acid;
L: linoleic acid

TABLE 3

Comparison of the levels of oleic acid (%) of sunflower seeds from F2 plants homozygous (Hm) for mutations 29065 and 29066 compared with F2 plants homozygous (Hm) for Pervenets mutation. Percentage oleic acid content for both Hm 29065 and 29066 was significantly higher than its respective Hm Pervenets counterpart.

| Population | Homozygous high oleic mutation | Average oleic acid % | Standard deviation | n |
|---|---|---|---|---|
| 20340 × 29065 | 29065 | 87.50 | 1.08 | 12 |
| | Pervenets | 82.86 | 5.38 | 18 |
| 20340 × 29066 | 29066 | 87.91 | 2.56 | 114 |
| | Pervenets | 86.26 | 2.64 | 90 |
| 20342 × 29065 | 29065 | 89.08 | 3.56 | 56 |
| | Pervenets | 75.81 | 11.15 | 57 |
| 20342 × 29066 | 29066 | 88.90 | 2.17 | 37 |
| | Pervenets | 87.17 | 2.08 | 41 | n: amount of F2 plants whose fatty acid composition was analyzed by gas chromatography.

Example 3

Sequencing of the Sunflower Genes that Encode a Polypeptide that has Oleate Desaturase Activity For sequencing studies, tissue samples were taken from each mutant with high oleic content, the genomic DNA was isolated and diluted to a stock concentration of 100 ng/μl. In order to obtain the coding sequence of the full oleate desaturase of high oleic mutants 29065 and 29066 and the original lines 29010 and HA89 (wild type) specific primers were designed for the gene. These were used to amplify by PCR (polymerase chain reaction) and generate two overlapping DNA segments (amplicons) that covered the entire OLD gene. The sequence of designed primers follows:

| | | |
|---|---|---|
| 1st amplicon (705 bp) | OLD1-F2 | GAAAAGTCTGGTCAAACAGTCAACAT (SEQ ID No: 7) |
| | OLD1-R2 | CCGATGTCGGACATGACTATC (SEQ ID No: 8) |
| 2nd amplicon (733 bp) | OLD1adv-F2 | AAATACTTTAACAACACAGTGGGC (SEQ ID No: 9) |
| | OLD1-R3 | CCAGAACCAGGACAACAGCCATTGTC (SEQ ID No: 10) |

All primers are specific for the desaturase oleate gene. The following conditions were used for polymerase chain reaction (PCR) in a final volume of 25 μl: 1× buffer (Invitrogen), 0.2 mm dNTPs (GE Healthcare), 2.5 mm MgCl$_2$ (Invitrogen), 0.2 μM of each primer, 0.5 μl of Platinum Taq (5 U/μl) (Invitrogen) and 100 ng of genomic DNA. KLA reaction by PCR was performed on a GeneAmp PCR System 9700 computer (Perkin-Elmer). The cycling conditions were: an initial denaturation step at 94° C. for 1 minute followed by 35 cycles consisting of 94° C. for 45 seconds, 57° C. for 45 seconds and 72° C. for 70 seconds, and a final elongation step 72° C. for 10 minutes.

In the case of the two mutants found with high content of oleic acid (29065 and 29066) amplification product could not be obtained when OLD1-F2 and OLD1-R2 primers were used. This led to postulate that these mutants possessed large segments of DNA inserted into the region comprised between these primers as a result of the mutagenic treatment with X-rays. This would mean that due to the large segment flanked by OLD1-F2 and OLD1-R2 primers, no amplification product could be obtained.

In order to establish the nucleotide sequence of the inserted segments, genomic libraries were generated for each of the mutants (29065 and 29066) in order to perform chromosome walking by PCR using the system GenomeWalker™ Universal Kit Protocol-at-a-Glance (Clontech) following the manufacturer's instructions.

Taking the nucleotide sequence of the oleate desaturase gene of lines HA89 and 29010 as a reference, genome walking was carried out both in a 5'- and 3'-sense for each mutant. The following specific primers were used for each of the mutants:

| Mutant 29065 | | |
|---|---|---|
| First time | OLD1-Walk3'-F1 | AACCACCCTTCACCATCGGCG (SEQ ID No: 11) |
| | OLD1-Walk3'-F2 | ACCCGTTCGTTCTCCTACGT (SEQ ID No: 12) |
| | OLD1-Walk5'-R1 | AGTGGCAGGCGAAACGGTCA (SEQ ID No: 13) |
| | OLD1-Walk5'-R2 | AGCCGAGAGTGAGAGTGACG (SEQ ID No: 14) |
| Second time | MUT29010HO-W2-5'-1 | ATGATCGCAGTCCCCAAAAG (SEQ ID No: 15) |
| | MUT29010HO-W2-5'-2 | CCAATCAGCCTACAATAACAA (SEQ ID No: 16) |
| | MUT29010HO-W2-3'-1 | AAGGGACGAGTAAAGACGAG (SEQ ID No: 17) |
| | MUT29010HO-W2-3'-2 | TCGTCGACCCATTGATAATC (SEQ ID No: 18) |

-continued

| | | Mutant 29066 | |
|---|---|---|---|
| First time | OLD1-Walk3'-F1 | AACCACCCTTCACCATCGGCG | (SEQ ID No: 11) |
| | OLD1-Walk3'-F2 | ACCCGTTCGTTCTCCTACGT | (SEQ ID No: 12) |
| | OLD1-Walk5'-R1 | AGTGGCAGGCGAAACGGTCA | (SEQ ID No: 13) |
| | OLD1-Walk5'-R2 | AGCCGAGAGTGAGAGTGACG | (SEQ ID No: 14) |
| Second time | MUTHA89HO-W2-5'-1 | GGAAAACAGGGTTATTGGCA | (SEQ ID No: 19) |
| | MUTHA89HO-W2-5'-2 | CAACAAAGCACGCACCCACA | (SEQ ID No: 20) |
| Third time | MUTHA89HO-W52-1 | TCATGGTAGTCAACTCCCTC | (SEQ ID No: 21) |
| | MUTHA89HO-W52-2 | CGCTTTCTTTCCTTCGGGCAA | (SEQ ID No: 22) |
| | MUTHA89HO-W32-1 | GCTAATCGTGATCCACAGGC | (SEQ ID No: 23) |
| | MUTHA89HO-W32-2 | GCCCACGACACTTACCAGA | (SEQ ID No: 24) |
| Fourth time | MUTHA89HO-W53-1 | CCCAACTCTATATTTTCAAG | (SEQ ID No: 25) |
| | MUTHA89HO-W53-2 | ACTTGAAAGTTTGGTTTCGG | (SEQ ID No: 26) |
| | MUTHA89HO-W33-1 | AGGGAACGGGGCAACATTTG | (SEQ ID No: 27) |
| | MUTHA89HO-W33-2 | GCCGCCTAACGAGAGACTT | (SEQ ID No: 28) |

Two microliters of each product that resulted from each PCR was analyzed by agarose gel electrophoresis and DNA concentration was estimated by comparison with the molecular weight marker Low DNA Mass Ladder (Invitrogen). The remainder product of the PCR was purified using a Gel Wizard® SV (Promega) and PCR Clean-Up System (Promega). The purified PCR products were sequenced using the BigDye® Terminator v3.1 Cycle Sequencing System (Applied Biosystems) following the manufacturer's instructions.

The files of the sequencing of the oleate desaturase obtained for each amplicon were assembled using CAPS Sequence Assembly Program (http://pbil.univ-lyon1.fr/cap3.php). The resulting DNA sequences of the oleate desaturase were aligned with the sequences of line HA89 deposited in GenBank (accession number AY802989) using Clustal W Program version 2.1 (http://www.clustal.org) identifying nucleotide insertions present in the mutants 29065 and 29066, which showed to have a size of 785 base pairs (bp) and 4872 bp, respectively. In addition, analysis of the mutated OLD sequences and their corresponding wild type showed that in the case of mutant line 29065 a 785-bp insertion was located at nucleotide position 310 of the coding region of the OLD gene while in the mutant line 29066 insertion of 4872 bp was located at nucleotide position 201.

The invention claimed is:

1. A sunflower plant comprising a mutation in an oleate desaturase gene yielding a truncated oleate desaturase protein, wherein the plant produces seeds with an oleic acid content between 80% and 95% with respect to the total percentage of fatty adds of the seed, wherein the truncated oleate desaturase protein consists of from 71 to 110 amino adds of the N-terminus of the wild type oleate desaturase protein, wherein the sunflower plant is homozygous for the mutation in the oleate desaturase gene yielding the truncated oleate desaturase protein, wherein the truncated oleate desaturase protein has lower enzyme activity compared to the wild type oleate desaturase protein, and wherein the oleate desaturase gene is a Delta-12 oleate desaturase gene.

2. The sunflower plant according to claim 1, wherein the truncated oleate desaturase protein comprises the amino acid sequence selected from the group consisting of SEQ ID NO: 1 and SEQ ID NO: 2.

3. The sunflower plant according to claim 2, wherein the truncated oleate desaturase protein comprises the amino acid sequence of SEQ ID NO: 1.

4. The sunflower plant according to claim 2, wherein the truncated oleate desaturase protein comprises the amino acid sequence of SEQ ID NO: 2.

5. A sunflower seed comprising a mutation in an oleate desaturase gene yielding a truncated oleate desaturase protein and having an oleic acid content between 80% and 95% with respect to the total percentage of fatty acids of the seed, wherein the truncated oleate desaturase protein consists of from 71 to 110 amino acids of the N-terminus of the wild type oleate desaturase protein, wherein the sunflower seed is homozygous for the mutation in the oleate desaturase gene yielding the truncated oleate desaturase protein, wherein the truncated oleate desaturase protein has lower enzyme activity compared to the wild type oleate desaturase protein, and wherein the oleate desaturase gene is a Delta-12 oleate desaturase gene.

6. The sunflower seed according to claim 5, wherein the truncated oleate desaturase protein comprises the amino acid sequence selected from the group consisting of SEQ ID NO: 1 and SEQ ID NO: 2.

7. The sunflower seed according to claim 6, wherein the truncated oleate desaturase protein comprises the amino acid sequence of SEQ ID NO: 1.

8. The sunflower seed according to claim 6, wherein the truncated oleate desaturase protein comprises the amino acid sequence of SEQ ID NO: 2.

9. A method of obtaining oil having an oleic add content between 85% and 95% with respect to the total fatty add content of the oil, comprising extracting oil from a sunflower seed comprising a mutation in an oleate desaturase gene yielding a truncated oleate desaturase protein and having an oleic add content between 80% and 95% with respect to the total percentage of fatty adds of the seed, wherein the truncated oleate desaturase protein consists of from 71 to 110 amino adds of the N-terminus of the wild type oleate desaturase protein, wherein the sunflower plant is homozygous for the mutation in the oleate desaturase gene yielding the truncated oleate desaturase protein, wherein the truncated oleate desaturase protein has lower enzyme activity compared to the wild type oleate desaturase protein, and wherein the oleate desaturase gene is a Delta-12 oleate desaturase gene.

10. The method according to claim 9, wherein the truncated oleate desaturase protein comprises amino acid sequence of SEQ ID NO: 1.

11. The method according to claim 9, wherein the truncated oleate desaturase protein comprises the amino acid sequence of SEQ ID NO: 2.

12. The sunflower plant according to claim 1, wherein the truncated oleate desaturase protein is encoded by an oleate desaturase gene having an insertion mutation.

13. The sunflower seed according to claim 5, wherein the truncated oleate desaturase protein is encoded by an oleate desaturase gene having an insertion mutation.

14. The method according to claim 9, wherein the truncated oleate desaturase protein is encoded by an oleate desaturase gene having an insertion mutation.

* * * * *